United States Patent [19]

Drake

[11] 4,152,351

[45] May 1, 1979

[54] PROCESS FOR THE HYDROGENATION OF OLEFINIC UNSATURATION IN AN ALIPHATIC DINITRILE

[75] Inventor: Charles A. Drake, Bartlesville, Okla.

[73] Assignee: Phillips Petroleum Company, Bartlesville, Okla.

[21] Appl. No.: 826,598

[22] Filed: Aug. 22, 1977

[51] Int. Cl.$^2$ .................. C07C 120/00; C07C 121/20
[52] U.S. Cl. .............. 260/465.8 R; 585/277; 562/592; 562/496; 260/465 R; 260/583 K; 260/583 P; 560/190; 568/903; 568/671
[58] Field of Search ......... 260/583 K, 583 P, 465.8 R

[56] References Cited

U.S. PATENT DOCUMENTS

| | | | |
|---|---|---|---|
| 2,166,971 | 7/1939 | Schmidt et al. | 260/583 K |
| 3,404,098 | 10/1968 | Stiles | 252/443 |
| 3,629,145 | 12/1971 | Morikawa et al. | 252/432 |
| 3,794,588 | 2/1974 | Stiles | 252/462 |

*Primary Examiner*—Joseph Paul Brust

[57] ABSTRACT

Aliphatic unsaturated material or compounds are hydrogenated. Specifically, unsaturated dinitrile, e.g., 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile and 2,6-dimethyl-4-methyleneheptanedinitrile, in a mixture resulting from reaction of isobutylene and acrylonitrile are hydrogenated in presence of a palladium hydrogenation catalyst disposed on an active alumina support also having disposed thereon an adjuvant selected from cerium, thorium, manganese, praseodymium, neodymium and samarium. A specific combination of adjuvants namely cerium together with lanthanum was found to improve the hydrogenation at low levels of cerium.

Other aliphatic compounds which can be hydrogenated according to the invention include among others ethylene, 1,3-butadiene, cinnamic acid, 5-methyl-4-nonenedicarboxylic acid, diethyl 5-methylenenonanedicarboxylate, etc.

Other catalyst supports are disclosed as are conditions for the hydrogenation.

4 Claims, No Drawings

PROCESS FOR THE HYDROGENATION OF OLEFINIC UNSATURATION IN AN ALIPHATIC DINITRILE

This invention relates to hydrogenation of olefinic unsaturation. More specifically, it relates to the catalytic hydrogenation of aliphatic, unsaturated compound in the presence of a palladium hydrogenation catalyst on a suitable support. Still more specifically, the invention relates to the use of applicable adjuvants for a palladium hydrogenation catalyst used to hydrogenate olefinic unsaturation. Further, the invention relates to the hydrogenation of aliphatic, unsaturated compounds containing nitrile groups.

In one of its concepts, the invention relates to the hydrogenation of an unsaturated dinitrile obtained by the reaction of isobutylene and acrylonitrile, e.g., 5-methyl-4-nonenedinitrile which is obtained in admixture with 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile and 2,6-dimethyl-4-methyleneheptanedinitrile. Such a mixture is referred to as "diadduct" for sake of convenience. In another of its concepts, the invention relates to the hydrogenation of a diadduct as herein described employing a supported palladium catalyst having an adjuvant selected from cerium, thorium, manganese, praseodymium, neodymium and samarium or a compound thereof, also as described herein. In a further concept still the invention provides the employment of such adjuvant within certain narrowly defined ranges also as further described herein.

It is known that palladium catalyst has a high hydrogenating activity but that its activity tends to decrease markedly, rapidly when used in hydrogenation, especially at elevated temperatures.

Accordingly, it is desirable to employ an adjuvant to extend the period of useful activity of the catalyst for purposes of hydrogenation.

Palladium on various supports and with various adjuvants has been advocated for hydrogenation as well as dehydrogenation in U.S. Pat. No. 3,629,145 issued Dec. 21, 1971, the disclosure of which is incorporated herein by reference. The patent deals with the hydrogenation of a benzene nucleus and with the dehydrogenation of cyclohexane to benzene.

The patent very generally and broadly discloses a number of carriers for palladium and that water-soluble salt of a metal having 3 or 4 valencies will serve to increase the thermal stability and therefore the catalytic activity of a support palladium hydrogenation catalyst. Column 4.

The hydrogenation of an unsaturated dinitrile in two steps to produce 5-methylnonane-1,9-diamine, an intermediate for the production of fiber grade polyamide and other polymeric materials, has been under active study for some time.

It is an object of this invention to provide a hydrogenation process. It is another object of this invention to provide a hydrogenation catalyst. It is a further object of this invention to provide a process for the hydrogenation of an aliphatic, unsaturated compound or material. It is a still further object of this invention to provide specifically active adjuvants for a supported palladium hydrogenation catalyst useful in the hydrogenation of an aliphatic, unsaturated compound, e.g., an unsaturated dinitrile. A further object of the invention, still, is to provide a specific combination of materials serving as adjuvant for a palladium hydrogenation catalyst.

Other aspects, concepts, objects and the several advantages of the invention are apparent from a study of this disclosure and the appended claims.

According to the present invention, an aliphatic, unsaturated compound or material is hydrogenated in the presence of a supported palladium catalyst having an adjuvant selected from one of the following metals: cerium, thorium, manganese, praseodymium, neodymium and samarium.

Also according to the present invention, in a specific instance, lanthanum has been found to exhibit adjuvant effect when used in combination with cerium at levels of cerium which are so low that alone the cerium does not exhibit adjuvant effect.

Still according to the invention, in its preferred form, it is applied to the hydrogenation employing a catalyst as herein described of a diadduct, also as herein described.

This invention relates to hydrogenation of olefinic unsaturation. Palladium hydrogenation catalysts often suffer a decline in activity during use with a resulting increase in olefinic unsaturation in the hydrogenation product. The use of the adjuvants of this invention with palladium hydrogenation catalysts slows the decline in catalytic activity without adversely affecting catalytic activity and allows longer hydrogenation runs between catalyst changes thus keeping up the desired hydrogenation activity without the presence of an excessive amount of olefinic unsaturation in the hydrogenation product.

Generally, the invention is concerned with using a palladium hydrogenation catalyst with adjuvant in the hydrogenation of a compound or material having olefinic unsaturation. A wide variety of compounds can be hydrogenated according to the invention. Broadly, these will contain from 2 to about 30 carbon atoms per molecule, preferably from about 4 to about 20 carbon atoms and at least one carbon-carbon double bond per molecule. They may contain more than one such carbon-carbon double bond per molecule, and in such instances, the double bonds may be conjugated or non-conjugated. Thus, for example, 1,3-butadiene is within the scope of compounds utilized in the instant invention. Suitable compounds can also contain one or more functional groups that are essentially unaffected by the reaction conditions as well as the olefinic unsaturation. Examples of such functional groups include the nitrile, hydroxy, alkoxy, carboxylic acid and carboxylic ester groups. The suitable compounds for use in the instant invention do not contain halogen or sulfur since these elements generally are effective poisons for the palladium hydrogenation catalyst.

Examples of aliphatic compounds or materials which can be hydrogenated according to the invention include ethylene, 1-hexene, 2-decene, 1-tetradecene, 1-eicosene, 1-triacontene, 2-methyl-2-pentene, 1,3-butadiene, 2,3-dimethyl-1,3-butadiene, 3,7-dimethyl-1,3,7-octatriene, 2-phenyl-1,3-butadiene, 2-diphenylethylene, 2-buten-1-ol, 9-octadecen-1-ol, 1-methoxy-1,3-butadiene, cinnamic acid, 5-methyl-4-nonenedicarboxylic acid, 5-methylenenonanediacarboxylic acid, diethyl 5-methyl-4-nonenedicarboxylate, diethyl 5-methylenenonanedicarboxylate, cinnamonitrile, 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl- 4-methyleneoctanedinitrile, 2,6-dimethyl-4-methyleneheptanedinitrile and the like.

The currently preferred hydrogenation substrate for use in the practice of the instant invention is the unsaturated dinitrile mixture obtained by the reaction of isobutylene and acrylonitrile. This unsaturated dinitrile mixture comprises 5-methyl-4-nonendinitrile, 2,4-dimethyl-4-octenedinitrile, 2,4-dimethyl-3-octanedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile.

The hydrogenation catalysts which are utilized in the instant invention are those based on palladium. For example, the catalyst can be elemental palladium, or compounds of palladium which are reducible by hydrogen to finely divided elemental palladium. Suitable hydrogen reducible compounds include the oxides, halides, nitrates, oxalates, acetates, carbamates, propionates, tartrates, hydroxides, and the like and mixtures thereof. Specific examples include elemental palladium, palladium oxide, palladium chloride, palladium nitrate, palladium oxalate, palladium acetate, and palladium hydroxide, and the like. The currently preferred palladium compounds for the preparation of the palladium catalyst of this invention are palladium acetate and palladium nitrate.

In the practice of this invention, it is preferable to employ catalytic amounts of elemental palladium on a solid catalyst carrier which does not deleteriously affect the catalytic hydrogenation process of this invention. Such supports include, for example, alumina, carbon, kieselguhr, silica, silica-alumina, calcium carbonate, asbestos, pumice, clays, and the like, and mixtures thereof. Alumina is presently the preferred support, it giving superior results for the hydrogenation of diadduct in absence of adjuvant.

When a support is employed in a batch hydrogenation, the amount of palladium on the support material generally will be in the range of about 0.05 to about 20, preferably 0.1 to 10 weight percent based on the weight of the total catalyst components. When a support is employed in a continuous process, the amount of palladium on the support material generally will be in the range of about 0.12 to about 10, preferably 0.15 to 5 weight percent based on the weight of the support. Examples of suitable catalysts for a batch process include 5 weight percent palladium on alumina and 10 weight percent palladium on charcoal. Examples of suitable catalysts for a continuous process include 0.5 weight percent palladium on alumina and 1 weight percent palladium on charcoal.

The amount of catalyst used in a batch process is in the range of broadly from 0.01 up to 30 and preferably from 0.05 up to 10 weight percent of catalyst, including the weight of the support, based on the compound being hydrogenated. The amount of catalyst used in a continuous process is such that a liquid hourly space velocity (LHSV) of broadly 0.1 to 30 and preferably 0.5 to 15 volumes of substrate plus diluent per volume of catalyst per hour will be attained.

According to the instant invention, the adjuvant is selected from compounds of cerium, thorium, manganese, praseodymium, neodymium, and samarium and is employed with a palladium hydrogenation catalyst thus to extend the useful life of the catalyst without adversely affecting catalytic activity during the hydrogenation of the above-described compounds. Suitable compounds of the adjuvant metals of the invention include the oxides, halides, nitrates, hydroxides, acetates, oxalates, carbamates, propionates, tartrates, and the like and mixtures. Currently preferred compounds for use in the practice of this invention are the acetates and nitrates.

Specific examples of suitable adjuvants include manganese diacetate, manganese dibenzoate, manganese carbonate, manganese dihydroxide, manganese dinitrate, manganese dichloride, manganese dibromide, manganese oxide, manganese dioxide, manganese trioxide, cerium triacetate, cerium trichloride, cerium trihydroxide, cerium (III) oxide, cerium (IV) oxide, cerium trinitrate, thorium hydroxide, thorium nitrate, thorium dioxide, thorium bromide, thorium carbonate, thorium oxalate, praseodymium acetate, praseodymium bromide, praseodymium chloride, praseodymium dioxide, praseodymium (III) oxide, neodymium acetate, neodymium bromide, neodymium nitrate, neodymium oxalate, neodymium oxide, neodymium chloride, samarium triacetate, samarium tribromide, samarium dichloride, samarium trichloride, samarium trihydroxide, samarium trinitrate, samarium (III) oxalate, samarium (III) oxide and the like. For economic reasons, it is not normally necessary that the adjuvant of this invention be of high purity. Thus, other materials that are not detrimental to the hydrogenation reaction can be present with the adjuvant.

A specific adjuvant, see Run 27, is a combination of lanthanum, of itself not effective, Runs 34 and 35, with cerium used at an otherwise noneffective level. See Run 2.

The approximate amount of adjuvant to be used in the practice of this invention is summarized below in terms of weight percent metal based on the weight of support.

| Adjuvant | Range (weight %)[a] | |
|---|---|---|
| | Broad | Preferred |
| Cerium | 0.2 to 8 | 0.3 to 6 |
| Thorium | 0.001 to 1.5 | 0.01 to 1 |
| Manganese | 0.001 to 1 | 0.01 to 0.5 |
| Praseodymium | 0.001 to 0.9 | 0.01 to 0.7 |
| Neodymium | 0.001 to 0.9 | 0.01 to 0.7 |
| Samarium | 0.001 to 2.0 | 0.01 to 1.5 |

[a] Weight percent adjuvant metal based on support weight

The mixture of adjuvant and palladium can be prepared in any convenient manner. For example, a mixture of palladium or a reducible compound of palladium and an adjuvant compound can be codeposited from a solution onto a support. The palladium or reducible compound of palladium and the adjuvant compound can also be deposited on the support separately in any order. The impregnated support can be calcined in air at temperatures of 300°–700° C. for times of about ½ hour to about 4 hours, and then reduced with hydrogen.

The hydrogenation reaction of this invention can be conducted in any conventional batch or continuous hydrogenation reactor. This reactor is preferably constructed of stainless steel to avoid possible corrosion.

The hydrogen pressure utilized in the hydrogenation according to the instant invention is broadly of the order of from about 50, preferably from about 100 to 5000 psig [0.7 to 35 mega Pascals (MPa)] and preferably 500 to 3000 psig (3.5 to 20.7 MPa). The temperature utilized in the hydrogenation of the instant invention is broadly from about 20° to 300° C. and preferably from 25° to 150° C. The time employed in a batch reaction in the hydrogenation process of the instant invention is not particularly critical and will generally range from a few minutes up to about 12 hours.

Preferably a diluent is used to facilitate the operation. It can be selected from aliphatic alcohols containing from 1 to 12 carbon atoms per molecule, unsubstituted acylic and unsubstituted cyclic ethers having from 4 to 12 carbon atoms per molecule, and saturated hydrocarbons having 4 to 12 carbon atoms per molecule. Examples of suitable diluents include methanol, ethanol, 2-propanol, 2-methyl-2-propanol, 1-octanol, pentane, decane, dodecane, cyclopentane, cyclohexane, cyclododecane, 1,3-dioxane, 1,4-dioxane, tetrahydrofuran, and the like and mixtures thereof. To facilitate handling of the reaction mixtures, the weight ratio of olefinically unsaturated reactant to diluent charged to the reactant zone is generally within the broad range of about 0.1:100 to about 50:100, and is preferably in the range of about 1:100 to 25:100.

The use of the above-described adjuvants with palladium hydrogenation catalysts according to this invention results in a slower decline in activity of the catalyst during the hydrogenation. Thus, the use of these adjuvants allows the longer use of the hydrogenation catalysts between catalyst changes while keeping a desirable low level of olefinic unsaturation in the hydrogenation product.

In all of the examples that follow, the aliphatic unsaturated material which was hydrogenated was an unsaturated dinitrile mixture obtained by the reaction of isobutylene and acrylonitrile. This unsaturated dinitrile mixture comprised 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. For convenience, the above mixture is described in the examples below as diadduct. The diadduct was hydrogenated to produce a saturated dinitrile that can be further hydrogenated to yield a valuable saturated diamine for use in the preparation of polyamides and other polymers, as used in production of fibers.

The catalyst support used was 8–14 mesh γ-alumina (Girdler Catalyst Company) and metal compounds used for the catalyst preparations were the acetates, nitrates, or chlorides and were commercial materials.

The catalysts were prepared by impregnating the support with the desired metal compound(s) from a suitable solvent, e.g. acetic acid or methanol, while evaporating the solvent in a rotary evaporator. The impregnated support was calcined in a furnace in an air-nitrogen mixture of 300° C. and reduced in the presence of hydrogen in the reactor. The amounts of catalyst and adjuvants are expressed in terms of weight percent metal based on the weight of support.

In each hydrogenation run, a 0.5″ (12.7 mm) diameter × 20″ (508 mm) length continuous reactor fitted with a steam heating system and temperature recorder was charged with 40 g. (about 45 ml) of the supported catalyst, flushed with nitrogen, flushed with hydrogen at a rate of 1 liter/min., and heated at 150° C. Unless otherwise stated, a mixture containing 90 weight percent methanol and 10 weight percent diadduct was fed to the reactor at a LHSV of about 3. Reactor conditions during the hydrogenation runs were 1500 psig (10.3 MPa) pressure, 100° C. temperature, and 1 liter/min. hydrogen flow.

Samples were collected from the reactor effluent at an initial time (after 2 to 4 hours of run time) and at a final time (after 18 to 20 hours of run time) and were analyzed for olefinic unsaturation by gas-liquid chromatography after removal of the diluent under reduced pressure. Changes in catalyst activity were indicated by the difference in olefinic unsaturation present in samples collected at the final and initial times during the run with small differences indicating small changes in catalyst activity. Catalyst activity was indicated by the level of olefinic unsaturation present in the hydrogenation product with low levels indicating high catalyst activity.

EXAMPLE I

A series of runs were conducted in which the olefinic unsaturation of diadduct was hydrogenated in the presence of catalysts containing various levels of palladium and cerium. The results of these runs are shown in Table I below.

Table I

| Run No. | Cerium, Weight % | Palladium, Weight % | Olefinic Unsaturation,[a] Weight % | |
|---|---|---|---|---|
| | | | Initial | Final |
| 1 | 0.0 | 0.5 | 0.9 | 2.3 |
| 2 | 0.1 | 0.5 | 4.0 | 4.0 |
| 3 | 0.5 | 0.5 | 0.6 | 0.8 |
| 4 | 1.0 | 0.5 | 0.4 | 0.8 |
| 5 | 5.0 | 0.5 | 1.0 | 1.8 |
| 6 | 10.0 | 0.5 | (b) | (b) |
| 7 | 0.5 | 0.0 | (c) | (c) |
| 8 | 0.5 | 0.1 | 1.4 | 5.6 |
| 9 | 1.0 | 0.2 | 0.4 | 0.8 |

[a] Weight % olefinic unsaturation in the hydrogenation product at the indicated sampling time during the run.
[b] Very little hydrogenation occurred.
[c] Essentially no hydrogenation occurred.

Run 1, which is considered a control run for this invention, had a difference in olefinic unsaturation of 1.4 weight percent between initial and final samplings. Invention runs 3,4,5, and 9 use cerium compounds as adjuvants and have smaller increases in olefinic unsaturation over this time period and higher catalytic activity in some cases than the control run. Levels of cerium outside the scope of this invention (runs 2 and 6) are detrimental to the hydrogenation of diadduct with palladium. Cerium in the absence of palladium (run 7) is not an efficient catalyst for the hydrogenation of the olefinic unsaturation of diadduct under the conditions utilized. The use of cerium with a low level of palladium (run 8) is not effective in preventing the rapid decline in activity during the hydrogenation run and this is believed to be a result of the low level of palladium.

These results demonstrate operability of this invention utilizing as set forth cerium compounds as adjuvants with a palladium hydrogenation catalyst to form a catalyst with high and relatively constant activity.

EXAMPLE II

Several runs were conducted in which the olefinic unsaturation of diadduct was hydrogenated in the presence of catalysts containing 0.5 weight percent palladium and various levels of manganese. The results of these runs are shown below along with run 1, which is included for comparison as a control run.

Table II

| Run No. | Manganese, Weight % | Olefinic Unsaturation,[a] Weight % | |
|---|---|---|---|
| | | Initial | Final |
| 1 | 0.0 | 0.9 | 2.3 |
| 10 | 0.1 | 0.5 | 0.9 |
| 11 | 1.0 | 0.8 | 2.4 |

[a]Weight percent olefinic unsaturation in the hydrogenation product at the indicated sampling time during the run.

Run 12, not included in the tables, utilized a catalyst containing 0.5 weight percent palladium, 5 weight percent silver, and 5 weight percent manganese. The diluent was 50:50 mixture of cyclohexane and t-butyl alcohol and the LHSV was about 2. After 5.5 hours in the hydrogenation run the product contained 6 weight percent olefinic unsaturation and after 44.5 hours in the run the product contained 18 weight percent olefinic unsaturation. Therefore, the presence of a high level of silver together with a high level of manganese is detrimental for the catalytic hydrogenation of the olefinic unsaturation of diadduct over palladium. The addition of manganese compounds at the 0.1 weight percent manganese level (run 10) resulted in a smaller increase in olefinic unsaturation in the hydrogenation product and a higher catalytic activity than in the control run 1. Higher manganese levels (run 11) are ineffective as adjuvants with palladium under the conditions used.

The results of these runs demonstrate operability of this invention as set forth utilizing manganese compounds as adjuvants with a palladium hydrogenation catalyst to form a catalyst with a high and relatively constant catalytic activity.

EXAMPLE III

Two runs were conducted in which the olefinic unsaturation of diadduct was hydrogenated in the presence of catalysts containing 0.5 weight percent palladium and various levels of thorium. The results of these runs are shown in Table III below along with run 1, which is included as a control run for comparison.

Table III

| Run No. | Thorium, Weight % | Olefinic Unsaturation,[a] Weight % | |
|---|---|---|---|
| | | Initial | Final |
| 1 | 0.0 | 0.9 | 2.3 |
| 13 | 0.5 | 1.0 | 1.0 |
| 14 | 2.0 | 1.5 | 6.5 |

[a]Weight percent olefinic unsaturation in the hydrogenation product at the indicated sampling time during the run.

The addition of thorium nitrate (at a 0.5 weight percent thorium level) to a palladium hydrogenation catalyst (run 13) resulted in a smaller increase in olefinic unsaturation than in the control run 1. Higher levels of thorium (run 14) are ineffective as an adjuvant with palladium under the conditions used.

The results of these runs demonstrate operability of this invention as set forth utilizing thorium compounds as adjuvants with a palladium hydrogenation catalyst to maintain a relatively constant catalytic activity during use.

EXAMPLE IV

Two runs were conducted in which the olefinic unsaturation of diadduct was hydrogenated in the presence of catalysts containing 0.5 weight percent palladium and various levels of praseodymium. The results of these runs are shown in Table IV below along with run 1, which is included as a control run for comparison.

Table IV

| Run No. | Praseodymium, Weight % | Olefinic Unsaturation,[a] Weight % | |
|---|---|---|---|
| | | Initial | Final |
| 1 | 0.0 | 0.9 | 2.3 |
| 15 | 0.5 | 0.5 | 1.5 |
| 16 | 1.0 | 2.0 | 5.9 |

[a]Weight percent olefinic unsaturation in the hydrogenation product at the indicated sampling time during the run.

The addition of praseodymium acetate (at a 0.5 weight percent praseodymium level) to a palladium hydrogenation catalyst (run 15) resulted in a smaller increase in olefinic unsaturation and a higher activity than in the control run 1. Higher levels of praseodymium (run 16) are ineffective as an adjuvant with palladium under the conditions used.

The results of these runs demonstrate operability of this invention as set forth utilizing praseodymium compounds as adjuvants with a palladium hydrogenation catalyst to maintain a higher and more constant catalytic activity.

EXAMPLE V

Two runs were conducted in which the olefinic unsaturation of diadduct was hydrogenated in the presence of catalysts containing 0.5 weight percent palladium and various levels of neodymium. The results of these runs are shown in Table V below along with run 1, which is included as a control run.

Table V

| Run No. | Neodymium, Weight % | Olefinic Unsaturation,[a] Weight % | |
|---|---|---|---|
| | | Initial | Final |
| 1 | 0.0 | 0.9 | 2.3 |
| 17 | 0.5 | 0.3 | 0.6 |
| 18 | 1.0 | 1.0 | 2.4 |

[a]Weight percent olefinic unsaturation in the hydrogenation product at the indicated sampling time during the run.

The addition of neodymium acetate (at a 0.5 weight percent neodymium level) to a palladium hydrogenation catalyst (run 17) resulted in a smaller increase in olefinic unsaturation and a higher activity than in the control run 1. Higher levels of neodymium (run 18) are ineffective as an adjuvant with palladium under the conditions used.

The results of these runs demonstrate operability of this invention as set forth utilizing neodymium compounds as adjuvants with a palladium hydrogenation catalyst to maintain a higher and more constant catalytic activity.

EXAMPLE VI

Several runs were conducted in which the olefinic unsaturation of diadduct was hydrogenated in the presence of catalysts containing 0.5 weight percent palladium and various levels of samarium. The results of these runs are shown in Table VI along with run 1, which is included as a control run.

Table VI

| Run No. | Samarium, Weight % | Olefinic Unsaturation,[a] Weight % | |
|---|---|---|---|
| | | Initial | Final |
| 1 | 0.0 | 0.9 | 2.3 |
| 19 | 0.5 | 0.8 | 1.3 |
| 20 | 1.0 | 0.8 | 1.9 |
| 21 | 1.5 | 0.9 | 0.6 |
| 22 | 2.5 | 1.7 | 3.7 |

[a]Weight percent olefinic unsaturation in the hydrogenation product at the indicated sampling time during the run.

The increases in olefinic unsaturation between initial and final samplings for the invention runs utilizing samarium compounds (0.5 to 1.5 weight percent samarium) as adjuvants (runs 19, 20, 21) were lower than in the control run 1. Higher levels of samarium (run 22) are ineffective as adjuvants for palladium under the reaction conditions used.

The results of these runs demonstrate operability of this invention as set forth utilizing samarium compounds as adjuvants with a palladium hydrogenation catalyst to maintain a higher and more constant catalytic activity.

EXAMPLE VII

Several runs were conducted in which the olefinic unsaturation of diadduct was hydrogenated in the presence of catalysts each containing 0.5 weight percent palladium, cerium compounds, and compounds containing manganese, praseodymium, samarium, or lanthanum. The results of these runs are presented in Table VII along with run 1 as a control for comparison.

Table VII

| Run No. | Cerium, Weight % | Other Component, Weight % | | Olefinic Unsaturation[a] Weight % | |
|---|---|---|---|---|---|
| | | | | Initial | Final |
| 1 | 0.0 | None | 0.0 | 0.9 | 2.3 |
| 23 | 0.1 | Mn | 0.1 | (b) | 1.0 |
| 24 | 0.5 | Pr | 0.5 | 0.8 | 0.5 |
| 25 | 1.0 | Pr | 1.0 | 0.6 | 2.4 |
| 26 | 0.5 | Sm | 0.5 | 0.6 | 2.0 |
| 27 | 0.1 | La | 0.1 | 0.1 | 0.2 |

[a]Weight percent olefinic unsaturation in the hydrogenation product at the indicated sampling time during the run.
[b]Lost sample.

The results of these runs show that in cases as illustrated (runs 23, 24, 25, and 26) there is no particular advantage in the use of mixtures of adjuvants over the use of the individual adjuvant. However, unexpectedly, in run 27 the use of lanthanum acetate, a compound outside the scope of this invention (see run 34 below), with cerium acetate improved the results of a hydrogenation using a low level of cerium (see run 2). A range in which such a result can be effected appears to be 0.05–0.5 weight % of each of cerium and lanthanum.

EXAMPLE VIII

Several runs were conducted in which the olefinic unsaturation of diadduct was hydrogenated in the presence of catalysts containing 0.5 weight percent palladium and compounds outside the scope of this invention. The results of these runs are presented in Table VIII along with run 1 for comparison as a control run.

Table VIII

| Run No. | Component, | Weight % | Olefinic Unsaturation[a] Weight % | |
|---|---|---|---|---|
| | | | Initial | Final |
| 1 | none | 0.0 | 0.9 | 2.3 |
| 28 | Al | 0.5 | 6.3 | 11.8 |
| 29 | Ni | 1.0 | (b) | (b) |
| 30 | Cr | 0.5 | 4.0 | 9.6 |
| 31 | Os | 0.1 | (b) | (b) |
| 32 | Ir | 0.1 | (b) | (b) |
| 33 | Zr | 1.0 | 4.1 | 8.5 |
| 34 | La | 0.1 | 1.0 | 2.6 |
| 35 | La | 1.0 | 3.0 | 5.4 |
| 36 | Yb | 0.5 | 1.9 | 5.1 |
| 37 | Yb | 1.0 | 1.5 | 2.6 |
| 38 | Gd | 0.5 | 1.1 | 5.4 |
| 39 | Gd | 1.1 | 1.9 | 2.1 |

[a]Weight percent olefinic unsaturation in the hydrogenation product at the indicated sampling time during the run.
[b]Very little hydrogenation occurred.

The results of these runs show that these components are ineffective (and actually detrimental in some cases) as adjuvants for palladium hydrogenation catalysts for maintaining stable activity without decreasing catalytic activity.

Reasonable variation and modification are possible in the scope of the foregoing disclosure and the appended claims to the invention, the essence of which is that there has been set forth a process for the hydrogenation of an aliphatic, unsaturated compound or material, especially a diadduct and that it has been found that a palladium catalyst supported, especially on an active alumina, e.g., an active alumina as described, the catalyst also having an adjuvant selected from those named herein and, in a special case, one of those named herein together with lanthanum, the adjuvants being used at concentrations given, will have a desirably longer activity life.

Reasonable variation and modification are possible in the scope of theforegoing disclosure and the appended claims to the invention, the essence of which is that there has been set forth a process for the hydrogenation of an aliphatic, unsaturated compound or material, especially a diadduct and that it has been found that a palladium catalyst supported, especially on an active alumina, e.g., an active alumina as described, the catalyst also having an adjuvant selected from those named herein and, in a special case, one of those named herein together with lanthanum, the adjuvants being used at concentrations given will have a desirably longer activity life.

I claim:

1. The hydrogenation of olefinic unsaturation in an aliphatic, unsaturated dinitrile compound which comprises under hydrogenation conditions of temperature and pressure, including the presence of hydrogen, contacting said dinitrile as the sole essential reactant present with a catalyst comprising palladium on an active support and having an adjuvant proportion of a compound of a metal selected from cerium, thorium, manganese, praseodymium, neodymium and samarium wherein the support is an active alumina and the weight percent of the adjuvant based upon the weight of the support is as follows:

| Adjuvant | Range (weight %) |
|---|---|
| Cerium | 0.2 to 8 |
| Thorium | 0.001 to 1.5 |

| Adjuvant | Range (weight %) |
| --- | --- |
| Manganese | 0.001 to 1 |
| Praseodymium | 0.001 to 0.9 |
| Neodymium | 0.001 to 0.9 |
| Samarium | 0.001 to 2.0 |

2. A hydrogenation according to claim 1 wherein the dinitrile is at least one of the following; 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile.

3. A process according to claim 1 wherein the hydrogen pressure is in the approximate range of a pressure of the order of from about 50 to about 5,000 psig and the temperature is in the range of from about 20° to 300° C.

4. A process according to claim 1 wherein the adjuvant portion of the catalyst is composed of cerium, 0.05–0.5 weight percent and lanthanum, 0.05–0.5 weight percent.

* * * * *